United States Patent [19]
Hosoi

[11] Patent Number: 5,502,519
[45] Date of Patent: Mar. 26, 1996

[54] OPTOMETRIC APPARATUS

[75] Inventor: Yoshinobu Hosoi, Gamagori, Japan

[73] Assignee: Nidek Co., Ltd., Japan

[21] Appl. No.: 168,998

[22] Filed: Dec. 20, 1993

[30] Foreign Application Priority Data

Jan. 12, 1993 [JP] Japan .................................. 5-020483

[51] Int. Cl.$^6$ ..................................................... A61B 3/10
[52] U.S. Cl. ........................ 351/204; 351/205; 351/208; 33/200
[58] Field of Search ..................................... 351/205, 211, 351/212, 247, 208, 204, 246, 245, 221; 33/200; 356/124, 127

[56] References Cited

U.S. PATENT DOCUMENTS 4,755,041  7/1988  Ishikawa et al. ........................ 351/211

*Primary Examiner*—William L. Sikes
*Assistant Examiner*—Hung Xuan Dang
*Attorney, Agent, or Firm*—Parkhurst, Wendel & Rossi

[57]                     ABSTRACT

An optometric apparatus for measuring optical characteristics of an eye to be examined comprising moving device for moving measuring section to adjust alignment with the eye to be examined, first and second deviation amount detecting devices for detecting deviation amount of the measuring section in a lateral and a vertical directions relatively to the eye at the time of measuring each of a left eye and a right eye to be examined, and correcting device for correcting data about an angle of astigmatic axis of the eye measured by the measuring section or interpupilary distance, based on the detected result obtained by the first deviation detecting device and the second deviation detecting device.

13 Claims, 5 Drawing Sheets

1

OPTOMETRIC APPARATUS

BACKGROUND OF THE INVENTION

1. Field of the Invention

The present invention relates to an optometric apparatus including an eye refractive measuring apparatus and a cornea shape measuring apparatus and others.

2. Description of Related Art

Generally, an eye refractive measurement apparatus and a cornea shape measuring apparatus are for measuring a direction of axis of an eye to be examined, such as astigmatic axis and principal meridian, and therefore need precise alignment between an eye to be examined and the apparatus unit. If the alignment between an eye to be examined and the apparatus unit is not precise, it will be inavoidable that the measured data obtained with such apparatus have errors therein.

In a conventional eye refractive measurement apparatus and the like, to effect alignment with an eye to be examined, utilized is a method of fixedly supporting the head of the examinee on a head or forehead support member so as to correspond with a direction of a reference axis of a measuring system.

The recent optometric apparatus utilizes a monitor to project image of the anterior part of the eye to be examined, accordingly, the alignment situation can be partially found based on the monitored image. For instance, U.S. Pat. No. 4,755,041 discloses such measuring apparatus.

There is also known an eye refractive power measuring apparatus with a system for measuring interpupilary distance which is a distance between each visual axes of a right and a left eyes of an examinee. For instance, U.S. Pat. No. 5,152,067 discloses such eye refractive power measurement apparatus in which the interpupilary distance is detected by measuring the moving distance of the measuring optical system from an alignment position with respect to an eye to another alignment position with another eye.

In apparatuses mentioned above, although at least the examinee's head is fixed on the head support member, there is no assurance that the right and left eyes of the examinee are certainly in a horizontal and, if anything, strictly, these eyes are commonly inclined off the horizontal. And further, according to differences among individuals, there are quite a few instances that the inclination of the eyes is remarkable. It is, therefore, difficult to obtain accurate data about astigmatic axis and principal meridian by the conventional apparatuses.

In the apparatus shown in U.S. Pat. No. 4,755,041, the anterior part of an eye is to be observed on a monitor, but it is just only a part around the pupil of the eye and therefore the examiner can find that both eyes are not in a horizontal only if an eye is extremely inclined.

And also, in the measurement of interpupilary distance taught in U.S. Pat. No. 5,152,067, when both eyes of the examinee are not in a horizontal, results obtained must include errors.

SUMMARY OF THE INVENTION

The present invention has been made in view of the above circumstances and has an object to overcome the above problems and to provide an optometric apparatus capable of measuring accurately optical characteristics of the an eye, for instance, an eye refractive power and a cornea shape and others, even if the examinee's head inclines to either side thereof relatively to the apparatus unit, namely, a right and a left eyes of the examinee are not positioned in a horizontal.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an optometric apparatus for measuring optical characteristics of an eye to be examined of this invention comprises moving means for moving measuring section to adjust alignment with an eye to be examined, first deviation amount detecting means for detecting deviation amount of the measuring section in a lateral direction relatively to the eye at the time of measuring each of a left eye and a right eye to be examined, second deviation amount detecting means for detecting deviation amount of the measuring section in a vertical direction relatively to the eye to be examined at the time of measuring each of a left eye and a right eye to be examined, and correcting means for correcting data about an angle of astigmatic axis of the eye measured by the measuring section, based on the result detected by the first deviation detecting means and the second deviation detecting means.

In the above apparatus, it is preferable to find an inclination angle of both eyes off a horizontal direction on the basis of deviation amount in a horizontal direction and a vertical direction between a right eye and a left eye of the examinee based on detected signals transmitted from the first deviation amount detecting means and the second deviation amount detecting means, thereby to calculate correctively an astigmatic axis angle.

In a second aspect of the present invention, an optometric apparatus for measuring optical characteristics of an eye to be examined comprises moving means for moving measuring section to adjust alignment with an eye to be examined, first deviation amount detecting means for detecting deviation amount of the measuring section in a lateral direction relatively to the eye to be examined at the time of measuring each of a left eye and a right eye to be examined, second deviation amount detecting means for detecting deviation amount of the measuring section in a vertical direction relatively to the eye to be examined at the time of measuring each of a left eye and a right eye to be examined, and arithmetic means for calculating interpupilary distance of the eyes to be examined based on the results detected by the first and the second deviation amount means respectively.

In the second construction, it is preferable to calculate interpupilary distance with Pythagoras' theorem formula on the basis of the deviation amount in the right and left and the vertical directions between a right and a left eyes, the deviation amount which is found based on the detected signal at the first and the second deviation amount detecting means.

In a third aspect, which is a more specific construction of the present invention, an optometric apparatus for measuring optical characteristics including eye refracting power and cornea shape and others of an eye to be examined, the apparatus comprises an apparatus unit disposed on a base, movably in the back and forth direction, in the right and left direction relatively to an examiner thereof, in which measuring optical system for measuring the optical characteristics of the eye to be examined is equipped, the measuring optical system being arranged movably in a vertical direction, a head support member and a forehead support member installed on the base to fixedly support the examinee's head, monitor means, installed in the apparatus unit, for projecting image of the anterior part of the eye to be examined and, at the same time, displaying results about eye refracting power, interpupilary and others, a first deviation amount detecting means for detecting moving amount of the apparatus unit in the lateral direction, a second deviation amount detecting means for detecting moving amount of the measuring optical system in the vertical direction, and an arithmetic means for finding an angle of the astigmatic axis and the interpupilary distance based on the deviation amount between a right and left eyes of the examinee obtained on the basis of the detected signals respectively at the first and the second deviation amount detecting means.

In the above construction, it is preferable that to find an angle of astigmatic axis and an interpupilary distance of the eye based on the detected signal at the first and second deviation detecting means.

According to the present invention, optical characteristics of the eye to examined including refractive power and cornea shape can be precisely measured even if the examinee's head inclined to one side thereof, namely, a right eye and a left eye of the examinee are not positioned in a horizontal.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of one preferred embodiment of an optometric apparatus embodying the present invention will now be given referring to the accompanying drawings.

Figure 1:
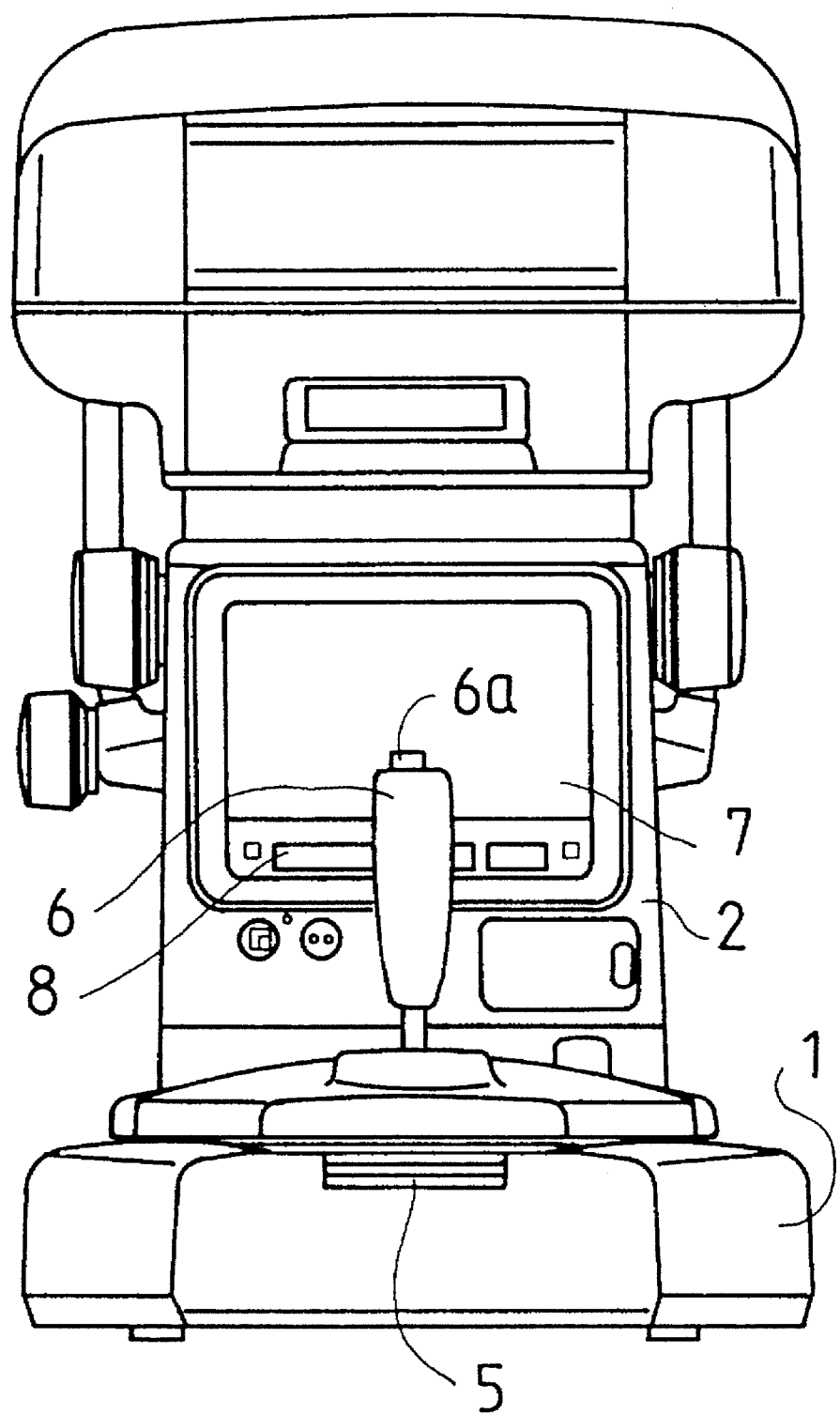
FIG. 1 is an external view in examiner's side, which shows an objective eye refractive power measurement apparatus in the first embodiment according to the present invention.
Figure 2:
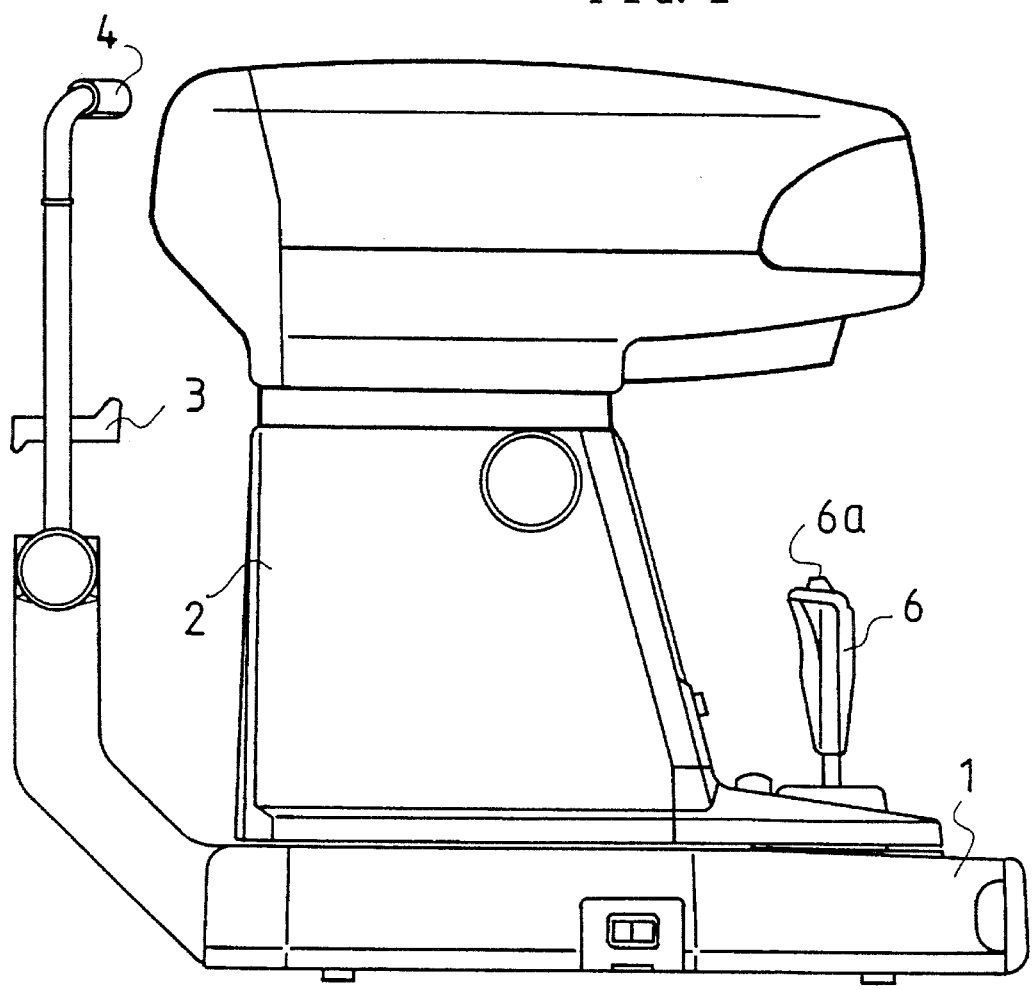
FIG. 2 is a left side view of the apparatus shown in FIG. 1.

In FIG. 1, the optometric apparatus comprises mainly a base 1 and an apparatus unit 2 which internally has a measuring optical system (an upper unit 17 and a lower unit 18 mentioned below) for measuring optical characteristic of an eye to be examined. Specifically, on the base 1, a head support member 3 and a forehead support member 4 are fixed at an end side of the base 1, both of which are for fixedly supporting the examinee's head opposing to the apparatus unit 2, and a printing section 5 is provided in another end side of the base 1. The apparatus unit 2 is provided with a joystick 6 to be used for operation to slidingly move the apparatus unit 2 in the back and forth and in the right and left directions along on the base 1, a television monitor 7 to project image of the anterior part of the eye to be examined and display measured results about interpupilary distance and others, a display screen 8 to display the value of refractive power of the eye to be examined, and a knob 19 to move up and down an optical axis of a measuring optical system. The sliding moving system with the joystick 6 and the vertical moving system with the knob 19 will be explained below.

Figure 3:
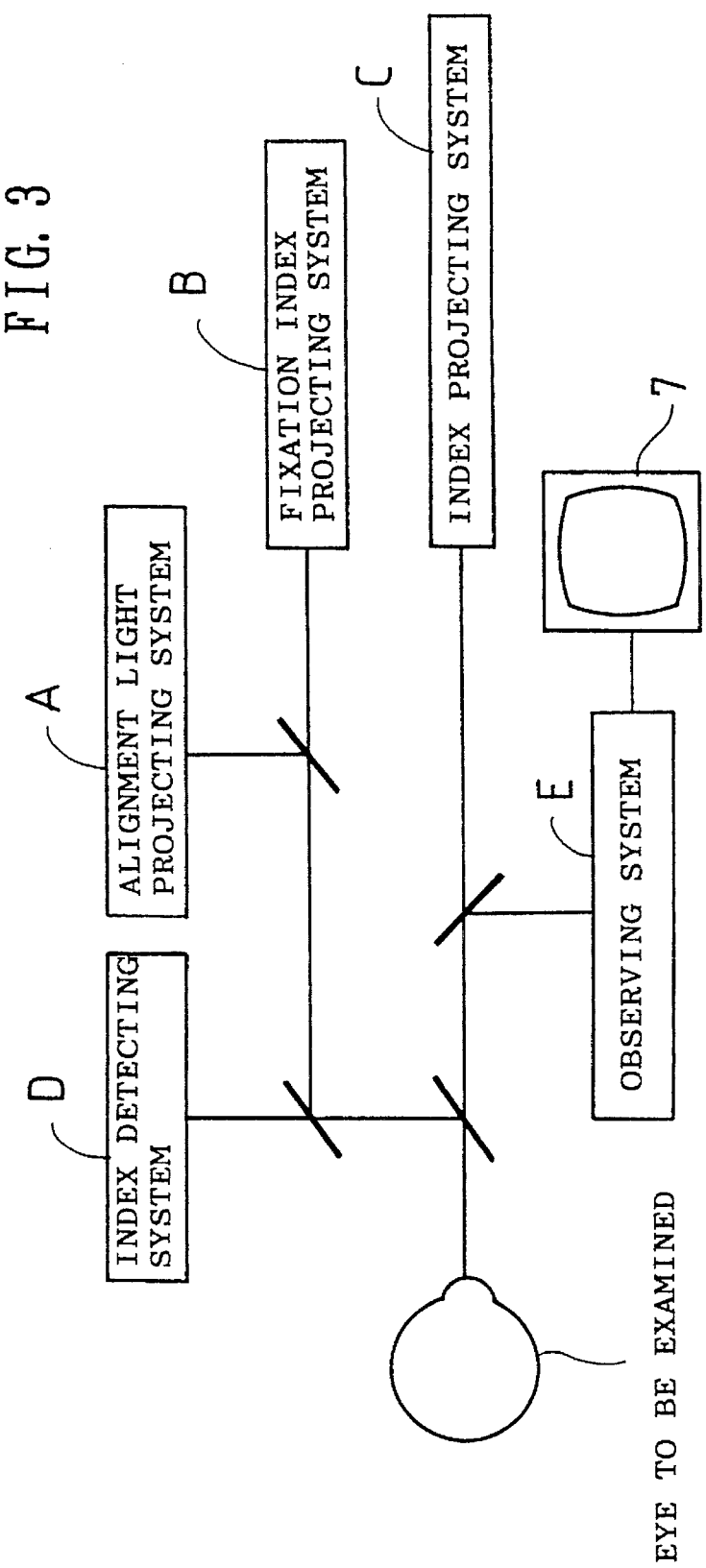
FIG. 3 is a block diagram to explain a measuring optical system included in the apparatus unit shown in FIG. 1.

In FIG. 3, the measurement optical system equipped inside the apparatus unit 2 is shown in a block diagram. The measurement optical system, as shown in FIG. 3, comprises an alignment light projecting system A, a fixation index projecting system B, an index projecting system C, an index detecting system D and an observing system E to which the television monitor 7 is connected. In such construction of the measuring optical system, the anterior part of the eye is photographed with a camera of the observing system and projected on the television monitor 7. And light beam emitted from the alignment light projecting system A is reflected by the cornea of the eye to be examined and then forms a cornea reflecting image thereon. Based on the cornea reflecting image, the examiner operates then the joystick 6 to move the apparatus unit 2 so that the eye to be examined and the cornea reflecting image are positioned with a predetermined relation on the monitor 7.

Next, the moving system to move the measuring section of the apparatus unit 2 will be explained hereinafter, referring to FIG. 4 and FIG. 5.

Figure 4:
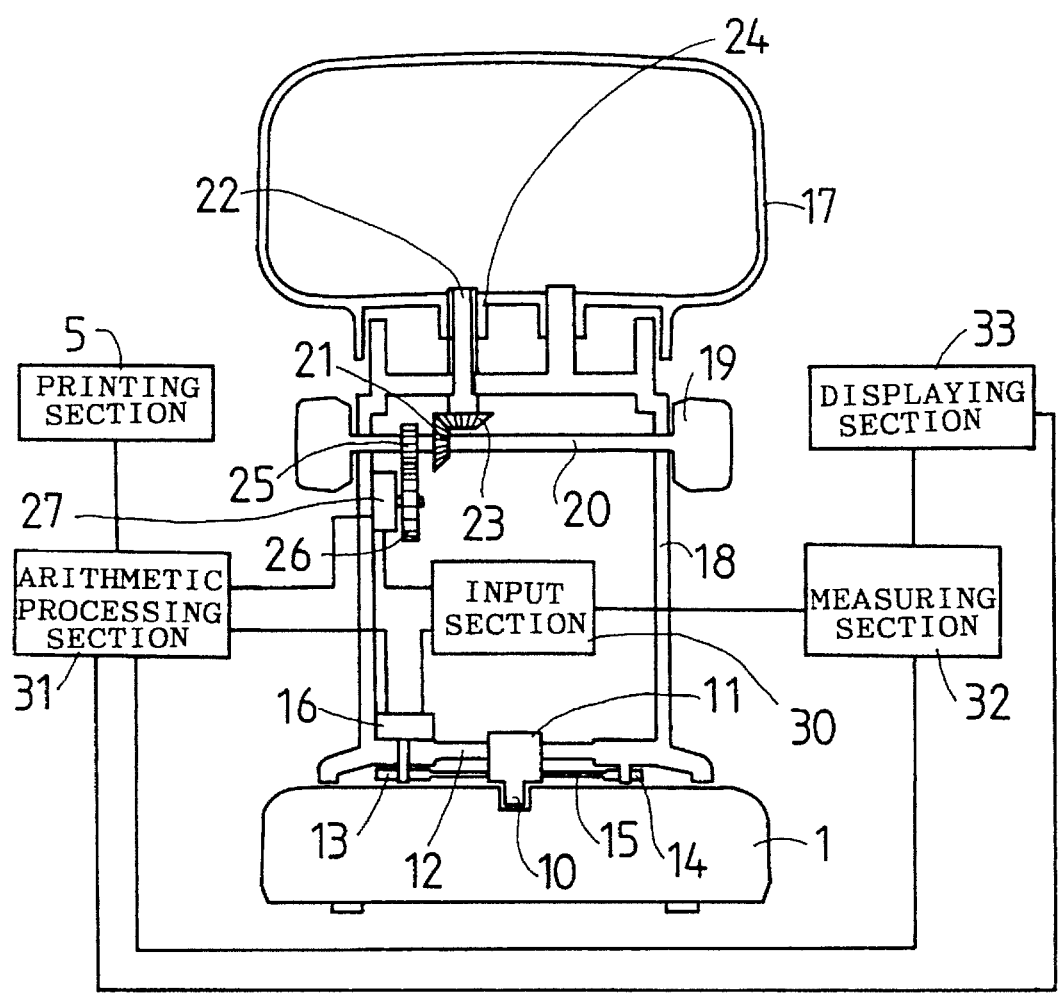
FIG. 4 is a constructive view to explain the moving system to move the measurement section of the apparatus in a vertical and in a horizontal directions.
Figure 5:
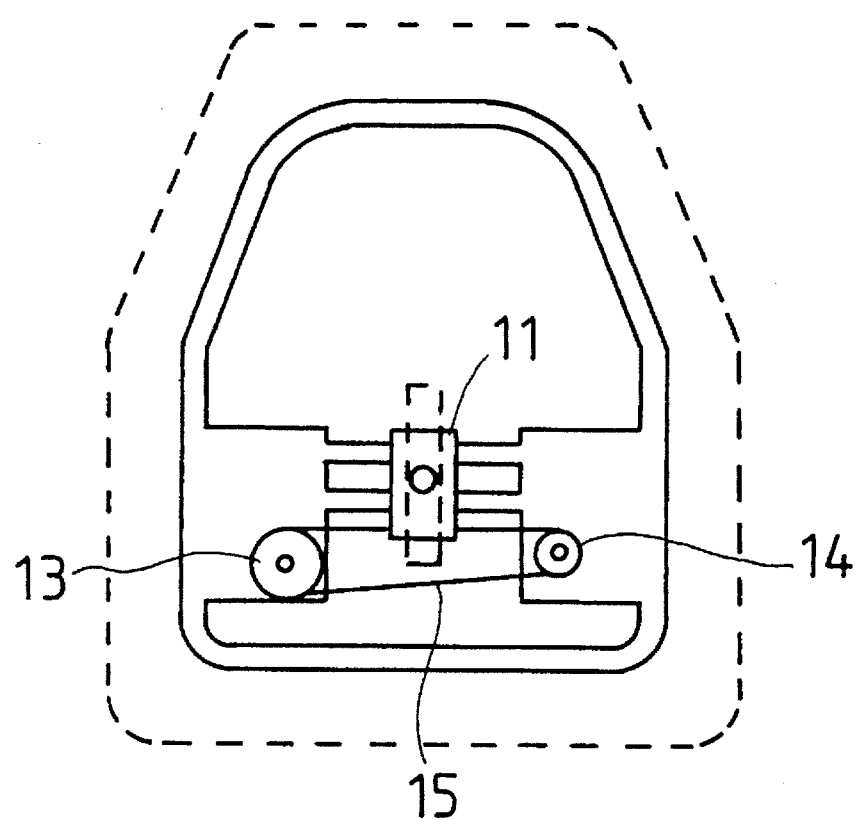
FIG. 5 is a schematic view bottom of the apparatus shown in FIG. 4.

As shown in FIGS. 4 and 5, a groove 10 is formed on the surface of the base 1, into which a fixed block 11 is fitted movably along a longitudinal direction of the groove 10. The fixed block 11 also supports axially two bars 12 through some bearings (not shown) so that the two bars 12 fixed at a bottom of the apparatus unit 2 may move through the fixed block 11 in the right and left direction of the apparatus unit 2. Accordingly, based on operation of the joystick 6, the above moving system consisting of the groove 10, the fixed block 11 and the two bars 12 can move the apparatus unit 2 slidingly on the base 1 in the back and force direction and in the right and left direction.

And further, as shown in FIG. 5, two pulleys 13 and 14 are installed on the bottom surface of the apparatus unit 2 and a wire 15 is put over the two pulleys 13 and 14. The wire 15 is partially fixed to the fixed block 11, and the two pulleys 13 and 14 are accordingly rotated through the wire 15 when the apparatus unit 2 is moved in the right and left direction relatively to the base 1. Then, a rotary encoder 16 provided in a rotating shaft of the pulley 13 detects the rotary number of the pulley 13, and based on which a moved distance of the apparatus unit 2 in the right and left direction is detected.

An upper unit 17 of the apparatus unit 2 in which the measuring optical system is equipped is supported on the lower unit 18 comprising a monitor and others so as to be movable in a vertical direction. Specifically, turning of the knob 19 installed to the lower unit 18 first rotates a driving shaft 20 and a bevel gear 21 fixed to the shaft 20, and further, the bevel gear 21 engaging with a bevel gear 23 fixed to a feed screw 22, the feed screw 22 rotates therewith in a female screw portion 24 formed at a bottom of the upper unit 17. The feed screw 22 and the female screw portion 24 of the upper unit 17 engage with each other, accordingly, the upper unit 17 is moved vertically to the lower unit 18.

A gear 25 is also fixed to the driving shaft 20, which engages with a gear 26 connected to a rotary encoder 27.

When rotary of the gear 25 is transmitted to the gear 26, the rotary encoder 27 detects the rotary number of the gear 26 and thereby the moved distance of the upper unit 17 in a vertical direction.

Control operation of detecting the moved distance of the apparatus unit 2 in the right and left direction and in the vertical direction.

Numeral 30 is an input section to which measurement mode and trigger signal and others are input. The input section 30, after received the trigger signal about an eye of the examinee, transmits an initial set signal to the rotary encoders 16 and 27. After that, pulse signals are output from the rotary encoders 16 and 27 respectively according to the movement of the apparatus unit 2, and counted through the processing circuit of arithmetic processing section 31. The deviation amount is thus detected based on the counted signals and then stored in a memory.

Measuring section 32 transmits picture data of the examinee's eye to a display section 33 and, at the same time, measured data to the arithmetic processing section 31 to process the data with the predetermined arithmetic operation.

In the optometric apparatus of the present embodiment, the optical measurement is performed to the eyes to be examined one each and the obtained result about a first eye is provisionally displayed at the display section 33. And, after measuring both eyes, the above result is corrected in accordance with the following process.

Assuming that X is a horizontal distance and Y is a vertical distance between a right and a left eyes, both distances which are detected at the rotary encoders 16 and 27, an inclined angle Z between the both eyes off the horizontal direction is characterized by the following formula (I);

$$Z = \tan^{-1}\frac{Y}{X} \qquad (I)$$

Based on the obtained inclined angle Z, an angle of the astigmatic axis of the eye which has been first obtained is corrected, for example, if the initial measured value is 90 degree and the value of Z is +10 degree, the angle of the astigmatic axis is corrected into 80 degree.

Measurement operation with the apparatus of above construction will be described as follow.

The head of the examinee, first, is fixedly supported on the head support member 3 and the forehead support member 4. While observing image of the anterior part of the eye to be examined displayed on the monitor 7, an examiner operates the knob 19 and the joystick 6 so that an alignment reticle and a cornea reflecting image are positioned with a determined relation with each other on the monitor 7. After alignment is completed, when a trigger button 6a provided at a top of the joystick 6 is pushed, refractive power of the examinee's eye is accordingly measured by the measuring section 32. The refractive power is then processed at the arithmetic processing section 31, and then displayed on the display section 33.

Following the above measurement of one eye, refractive power of another eye of the examinee is measured. Also in this measurement, same alignment operation as the former is performed with the knob 19 and the joystick 6. The rotary encoders 16 and 27 receive the initial set signals following the first trigger signal. And the rotary encoders 16 and 27 detect the subsequent deviation amount in a lateral and in a vertical directions respectively. When such alignment operation is completed, the trigger button 6a is pushed and thereby refractive power of the eye is measured. The measured value of the refractive power is similarly processed in the arithmetic processing section 31 and displayed on the display section 33.

The rotary encoders 16 and 27 detect the deviation amount in the lateral and the vertical directions between the trigger signals generated by the trigger button 6a with respect to the right and left eyes of the examinee respectively. If the deviation amount in the vertical direction exceeds the designated range, indication of necessity to correct the measured value is displayed on the monitor 7 in order to call the examiner's attention. And the data of refractive power, which is corrected in accordance with the above formula (I), is displayed on the display section 33. Instead of being displayed on the display section 33, the corrected data may be displayed only on the printing section.

The interpupilary distance PD is found based on the deviation amount in the vertical and the lateral directions as the following formula (II);

$$PD = \sqrt{X^2 + Y^2} \qquad (II)$$

Such calculating the above interpupilary distance PD may be processed only if the deviation amount in the vertical direction exceeds the designated range.

The present invention may be embodied in other specific forms without departing from the spirit or essential characteristics thereof. In the above embodiment, the present invention is applied to an objective refractive power measurement apparatus, and further, it may be utilized to correct principal meridian direction in a cornea shape measuring apparatus as disclosed in U.S. Pat. No. 5,212,507.

The above embodiment embodying the present invention may also be varied. Specifically, various means may be applied as means for detecting the deviation amount, for instance, positions of eyes to be examined are detected through two-dimensional CCD and the like and then, based on the detected position, position of measuring optical, axis is moved by pulse motor and the like, thereby the deviation amount is moved based on the moved amount of the measuring optical axis. And, in a measurement apparatus in which both eyes can be synchronously measured, the deviation amount may be detected by detecting each position of measurement optical axes of the eyes.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An optometric apparatus for measuring optical characteristics of an eye to be examined comprising:

moving means for moving measuring section to adjust alignment with an eye to be examined;

first deviation amount detecting means for detecting deviation amount of the measuring section in a lateral direction relatively to the eye at the time of measuring each of a left eye and a right eye to be examined;

second deviation amount detecting means for detecting deviation amount of the measuring section in a vertical direction relatively to the eye to be examined at the time of measuring each of a left eye and a right eye to be examined; and correcting means for correcting data about an angle of astigmatic axis of the eye measured by the measuring section, based on the result detected by the first deviation detecting means and the second deviation detecting means.

2. An optometric apparatus according to claim 1, wherein the correcting means is to find an inclining angle off the horizontal between a right and a left eyes on the basis of the deviation amount in the lateral and the vertical directions which are obtained based on the detected signals at the first and the second deviation amount detecting means respectively, whereby the angle of the astigmatic axis is calculated and corrected.

3. An optometric apparatus according to claim 1, further comprising monitor means to project image of the anterior part of the eye to be examined.

4. An optometric apparatus according to claim 3, wherein the measuring section is arranged movably in a vertical direction relatively to the monitor means.

5. An optometric apparatus according to claim 1, further comprising output means to print out measured data of optical characteristics of the eye to be examined.

6. An optometric apparatus for measuring optical characteristics of an eye to be examined comprising:

moving means for moving measuring section to adjust alignment with an eye to be examined;

first deviation amount detecting means for detecting deviation amount of the measuring section in a lateral direction relatively to the eye to be examined at the time of measuring each of a left eye and a right eye to be examined;

second deviation amount detecting means for detecting deviation amount of the measuring section in a vertical direction relatively to the eye to be examined at the time of measuring each of a left eye and a right eye to be examined; and arithmetic means for calculating interpupilary distance of the eyes to be examined based on the results detected by the first and the second deviation amount means respectively.

7. An optometric apparatus according to claim 6, wherein the arithmetic means is to calculate the interpupilary distance with Pythagoras' theorem formula on the basis of the deviation amount in the lateral and the vertical directions between the both eyes, the deviation amount being obtained based on detected signals at the first and the second deviation amount detecting means.

8. An optometric apparatus according to claim 6, further comprising monitor means to project image of the anterior part of the eye to be examined.

9. An optometric apparatus according to claim 8, wherein the measuring section is arranged movably in a vertical direction relatively to the monitor means.

10. An optometric apparatus according to claim 6, further comprising output means to print out measured data of optical characteristics of the eye.

11. An optometric apparatus for measuring optical characteristics including eye refracting power and cornea shape and others of an eye to be examined, the apparatus comprising:

an apparatus unit disposed on a base, movably in the back and forth direction, in the right and left direction relatively to an examiner thereof, in which measuring optical system for measuring the optical characteristics of the eye to be examined is equipped, the measuring optical system being arranged movably in a vertical direction;

a head support member and a forehead support member installed on the base to fixedly support the examinee's head;

monitor means, installed in the apparatus unit, for projecting image of the anterior part of the eye to be examined and, at the same time, displaying results about eye refracting power, interpupilary and others;

a first deviation amount detecting means for detecting moving amount of the apparatus unit in the lateral direction, a second deviation amount detecting means for detecting moving amount of the measuring optical system in the vertical direction; and, an arithmetic means for finding an angle of the astigmatic axis and the interpupilary distance based on the deviation amount between a right and left eyes of the examinee obtained on the basis of the detected signals respectively at the first and the second deviation amount detecting means.

12. An optometric apparatus according to claim 11, wherein said optical measuring system equipped inside the apparatus unit is movable in a vertical direction relatively to the monitor means.

13. An optometric apparatus according to claim 11, further comprising an output means for printing out the measured data about the optical characteristic of the eye.

* * * * *